US009117616B2

(12) United States Patent
Sohn

(10) Patent No.: US 9,117,616 B2
(45) Date of Patent: Aug. 25, 2015

(54) DIELECTRIC BARRIER DISCHARGE-TYPE ELECTRODE STRUCTURE FOR GENERATING PLASMA HAVING CONDUCTIVE BODY PROTRUSION ON ELECTRODES

(71) Applicant: SP TECH CO., LTD., Gyeonggi-do (KR)

(72) Inventor: Hee Sik Sohn, Seoul (KR)

(73) Assignee: SP TECH CO., LTD., Gyeonggi-do (KR)

( * ) Notice: Subject to any disclaimer, the term of this patent is extended or adjusted under 35 U.S.C. 154(b) by 0 days.

(21) Appl. No.: 14/414,517

(22) PCT Filed: Jun. 27, 2013

(86) PCT No.: PCT/KR2013/005706
§ 371 (c)(1),
(2) Date: Jan. 13, 2015

(87) PCT Pub. No.: WO2014/010851
PCT Pub. Date: Jan. 16, 2014

(65) Prior Publication Data
US 2015/0137677 A1    May 21, 2015

(30) Foreign Application Priority Data

Jul. 13, 2012    (KR) .......................... 10-2012-0076391

(51) Int. Cl.
*H01J 1/88*     (2006.01)
*H01J 19/42*    (2006.01)
(Continued)

(52) U.S. Cl.
CPC ... *H01J 1/88* (2013.01); *A61L 2/14* (2013.01); *A61L 9/22* (2013.01); *H01J 1/02* (2013.01); *H05H 1/2406* (2013.01); *H05H 2001/2412* (2013.01); *H05H 2001/2437* (2013.01)

(58) Field of Classification Search
CPC ..................... H01J 37/32091; H01J 37/32541; H01J 37/32568; H01J 37/32559; H01J 37/32; H01J 37/32009; H01J 37/32036; H01J 37/32532
USPC ......................................................... 313/268
See application file for complete search history.

(56) References Cited

U.S. PATENT DOCUMENTS 4,954,320 A    9/1990 Birmingham et al.
5,236,627 A    8/1993 Hannecart et al.
(Continued)

FOREIGN PATENT DOCUMENTS

JP    2009-78266        4/2009
KR    10-2002-0046093   6/2002
(Continued)

OTHER PUBLICATIONS
International Search Report for PCT/KR2013/005706, mailed Sep. 4, 2013.

*Primary Examiner* — Thomas A Hollweg
*Assistant Examiner* — Kevin Quarterman
(74) *Attorney, Agent, or Firm* — Barnes & Thornburg LLP

(57) ABSTRACT

Provided is a dielectric barrier discharge-type electrode structure for generating plasma. The electrode structure, according to the present invention, comprises: an upper conductive body electrode and a lower conductive body electrode; at least one conductive body electrode protrusion portion, which is formed on at least one surface of the upper conductive body electrode and/or the lower conductive body electrode; a dielectric layer which is formed on at least one of the inner surfaces of the upper conductive body electrode and the lower conductive body electrode that face each other, so as to have a substantially uniform thickness; and a specific gap (d) which is formed between the upper and lower conductive body electrodes and the dielectric layer, or between dielectric layers, due to the protruding effect of the conductive body electrode protrusion portion when the upper conductive body electrode and the lower conductive body electrodes come into close contact, wherein the plasma is generated by applying a pulse power or an alternating power to the upper conductive body electrode and the lower conductive body electrode.

17 Claims, 11 Drawing Sheets

(51) Int. Cl.
*H05H 1/24* (2006.01)
*H01J 1/02* (2006.01)
*A61L 9/22* (2006.01)
*A61L 2/14* (2006.01)

(56) References Cited

U.S. PATENT DOCUMENTS

| | | | |
|---|---|---|---|
| 5,236,672 A | 8/1993 | Nunez et al. | |
| 5,843,288 A | 12/1998 | Yamamoto | |
| 2006/0196762 A1* | 9/2006 | Miki et al. | 204/157.3 |
| 2007/0037408 A1* | 2/2007 | Tachibana et al. | 438/778 |
| 2007/0210713 A1* | 9/2007 | Lomaev et al. | 313/631 |
| 2008/0118410 A1* | 5/2008 | Furukawa et al. | 422/186.03 |
| 2009/0208387 A1* | 8/2009 | Masuda et al. | 422/186.04 |
| 2010/0068413 A1* | 3/2010 | Lee | 427/569 |
| 2011/0048025 A1* | 3/2011 | Ginn et al. | 60/770 |
| 2011/0260732 A1* | 10/2011 | Shinada et al. | 324/464 |
| 2012/0080412 A1* | 4/2012 | Holbeche et al. | 219/121.48 |
| 2013/0154658 A1* | 6/2013 | Shinada et al. | 324/464 |
| 2014/0138030 A1* | 5/2014 | Sawada et al. | 156/345.29 |

FOREIGN PATENT DOCUMENTS

| | | |
|---|---|---|
| KR | 10-2003-0088710 | 11/2003 |
| KR | 10-2006-0017191 | 2/2006 |
| KR | 10-2007-0076939 | 7/2007 |
| KR | 10-0747178 | 8/2007 |
| KR | 10-2009-009675 | 1/2009 |
| KR | 10-2009-0086761 | 8/2009 |
| KR | 10-2009-0097340 | 9/2009 |
| KR | 10-0924649 | 10/2009 |
| KR | 10-2012-0065224 | 6/2012 |
| KR | 10-2013-0085320 | 7/2013 |

* cited by examiner (a)  (b)

(a)          (b)          (c)

DIELECTRIC BARRIER DISCHARGE-TYPE ELECTRODE STRUCTURE FOR GENERATING PLASMA HAVING CONDUCTIVE BODY PROTRUSION ON ELECTRODES

CROSS-REFERENCE TO RELATED APPLICATIONS

This application is a national stage entry under 35 USC §371(b) of PCT International Application No. PCT/KR2013/005706, filed Jun. 27, 2013, and claims the benefit of Korean Patent Application No. 10-2012-0076391, filed on Jul. 13, 2012, both of which are expressly incorporated by reference herein.

TECHNICAL FIELD

The present invention relates to a plasma electrode structure applied to an air cleaning system and the like and, more particularly, to a dielectric barrier discharge (DBD)-type plasma generating electrode structure which generates a plasma in a gaseous fluid such as air such that electrons, ions, ultraviolet rays, etc. generated at this time react with bacteria and odor molecules to exhibit harmful gas decomposition and sterilization, thereby purifying the air present in an air conditioner, a refrigerator, a washing machine, a vehicle, etc.

BACKGROUND ART

With the increasing importance of indoor air cleaning, various methods for simultaneously removing particles and gaseous substances present in the room have been developed. These air cleaning techniques include filter type, electrostatic precipitation type, plasma type, UV/photocatalytic type, hybrid type with several methods, etc.

Among others, it is known that the air cleaning method using plasma has a significant effect on the removal of contaminants. Electrons and radicals generated by a plasma discharge phenomenon remove most harmful gases such as volatile organic compounds (VOCs), NOx, CFCs, etc. due to high oxidation and exhibit excellent sterilizing effect, and oxygen anions combine with pollen, fine dust, etc. that cause allergic symptoms and allow these particles to agglomerate together to be easily removed.

The plasma discharge can be divided into corona discharge and dielectric barrier discharge.

Corona Discharge

A corona discharge electrode comprises a pointed cathode and a flat counter electrode. When a negative high voltage is applied to the cathode, electrons emitted from the cathode collide with particles to generate cations, and the generated cations are accelerated toward the cathode by electrical attraction and collide with the cathode to emit high-energy secondary electrons. These high-energy electrons and heavy particles cause an inelastic collision to generate chemically reactive species. FIG. 1 shows a typical structure of a corona discharge electrode, in which (a) shows a single needle electrode type and (b) shows a multiple needle electrode type.

The corona discharge electrode is easy to manufacture and has a simple structure, resulting in low prices. However, a large amount of ozone is generated during the discharge and its long lifespan does harm to the human body. Moreover, the generated anions have a very short lifespan, and the amount of ultraviolet rays produced is also small, resulting in a low sterilizing effect.

Furthermore, the plasma volume is very small, and thus the plasma treatment area is limited to a small area. Accordingly, the number of cathodes has been increased to increase the treatment area, but even in this case, a micro arc (streamer) is generated in a direction perpendicular to the electrode gap, and this streamer is generally focused on the same spot, localizing the treatment effect.

To avoid these problems, a dielectric barrier discharge has been proposed.

Dielectric Barrier Discharge (DBD)

A dielectric barrier can generate a high-power discharge at atmospheric pressure, does not require a complicated pulse power supply, and thus is widely used in the industry, particularly for ozone generation, $CO_2$ laser, UV source, pollution treatment, etc.

FIG. 2 shows a typical structure of a dielectric barrier plasma electrode. As show in FIG. 2, a dielectric barrier discharge (DBD) apparatus comprises two parallel metal electrodes. At least one electrode is coated with a dielectric layer. When an insulator is used, in the case of DC power, the flow of current through the electrode is impossible, and thus an AC power is used to generate the plasma. For stable plasma generation, the gap between the electrodes is limited to several millimeters, and a plasma gas flows through the gap.

The dielectric barrier discharge is also called a "silent discharge" because there is no discharge that locally causes a pulse or noise. The discharge is ignited by a sine function or pulse-type power. Depending on the composition of a working gas and the voltage and frequency, the discharge is a filament-type or glow-type discharge. The filament-type discharge is formed with a micro discharge or streamer that develops on the surface of the dielectric layer.

Here, the dielectric layer serves to block a reverse current and avoid a transition into an arc, thus enabling the operation in a continuous pulse mode. Moreover, the electrons are accumulated on the dielectric surface, and the streamers are distributed randomly on the surface, thus inducing a uniform discharge.

The dielectric barrier discharge (DBD) has several variations as follows:

Surface Discharge

As shown in FIG. 3, a metal electrode such as silver is provided on the surface of a ceramic plate, and a plate-type counter electrode is provided inside the ceramic plate. Then, when an AC current is applied between the two electrodes, a glow discharge is generated around the stripe-shaped electrode on the ceramic plate. This discharge is distinguished from the silent discharge, which will be described later, due to the generation of noise during the discharge. This method is effective for the generation of ozone, and a related prior art includes Korean Patent No. 10-0747178.

Silent Discharge (Volume Discharge)

The silent discharge is a typical structure of the dielectric barrier plasma electrode, in which an insulator such as glass is put on one or both electrodes parallel to each other with a gap of several millimeters (mm), and when an AC voltage is applied thereto, small pulse discharges occur in countless numbers without causing the glow discharge. This is called the silent discharge and is widely used in the industrial fields such as the removal of harmful gases due to the generation of active ions.

FIG. 4(a) shows a plate-type dielectric barrier electrode structure. According to this structure, the electric field applied to the surface is uniform, and thus charges are non-uniformly accumulated in the dielectric with a specific statistical distribution pattern, which induces a streamer discharge, not the glow discharge, thus reducing the amount of ultraviolet rays produced.

FIG. 4(b) shows a mesh-type DBD structure, a variation of the plate-type DBD. According to this structure, a mesh electrode is used instead of a typical plate electrode such that the concentration of electrons in the plasma is uniformly distributed due to electric field enhancement in a reactor as well as the geometric structure of the mesh electrode, unlike the typical streamer discharge, thus generating a multi-glow discharge with excellent uniformity and efficiency of plasma. As a result, compared to the existing corona discharge and typical DBD discharge, it is possible to generate a plasma with a large amount of ultraviolet rays and a large amount of active species such as OH radicals, atomic oxygen (O), etc. However, this structure tends to generate noise and exerts high counter-pressure against the flow of fluid due to a high discharge voltage and a narrow gap between the electrodes. Accordingly, as disclosed in Korean Patent Publication No. 10-2002-0046093, it is necessary to extend the electrodes having the same structure in parallel to increase the processing capacity, but the structure is complicated, and the generation of counter-pressure cannot be avoided due to the cross-sectional area of the electrodes.

As a method for solving the problem of the generation of the counter-pressure, Korean Patent Publication No. 10-2009-0097340 discloses a method of forming a through hole that penetrates an electrode. This through hole is not a specific structure that is used only in this publication, but is disclosed in various documents and is widely used to avoid the counter-pressure. Moreover, a method of forming a gap between two electrodes used in this publication employs macroscopic units in millimeters (mm) or more by the structural design of the mechanism, which corresponds to the typical method, not a micro gap method, and this method has various problems such as requiring a high voltage as an applied voltage.

FIG. 4(c) shows another electrode structure, called a micro cap discharge, which generates a strong plasma using a very small discharge gap between electrodes, which is several tens to hundreds of micrometers. This method generates a loud noise and a large amount of ozone during discharge, and thus it is necessary to control the applied voltage so as not to generate the streamer. Moreover, the probability of contact between air and active species in the plasma section is much higher than other structures, and thus large amounts of species effective for the air cleaning and sterilization are generated, thus providing a good sterilizing effect and generating less noise and ozone, compared to the mesh-type DBD. A related prior art includes Korean Patent Publication No. 10-2006-0017191.

However, according to this method, it is necessary to form a micro gap between the electrodes, which complicates the structure, and there is a method of supporting the structure with an insulator from the outside of the metal electrode to implement the gap.

Moreover, in the case of Japanese Patent No. 2009-78266, a through hole is used in an electrode to facilitate the flow of fluid, and an insulating spacer (a spacing device) for forming a gap between electrodes is inserted into the electrodes. However, in the case of the above method, in order to form the spacer, a ceramic insulator, on the electrode, it is necessary to form a dielectric layer on the electrode, form a pattern for the insulating spacer thereof, and then form an insulating layer thereon, and thus there are problems that the process is complicated, the control of the height of the spacer is significantly difficult to achieve, and the production cost is significantly increased.

Similarly, in the case of Korean Patent Publication Nos. 10-2012-006402 and 10-2012-0065224, the use of the through hole is the same as above and, in the case of the formation of the gap between the electrodes, a natural surface unevenness occurring during the formation of the dielectric is used as a gap, without forming the gap using a spacer. However, in the case of this surface unevenness, the shape is random, and thus the gap between the electrodes is different for each position, which makes it possible to uniformly control the electrode properties, and a large amount of ozone is generated, which are very problematic.

Meanwhile, an electrode structure, in which pallets or beads having dielectric properties are filled in a tubular reactor or the fillers are coated with a catalyst, is also used. However, according to these methods, a loss in pressure occurs due to the dielectric filled in the reactor, and when particulate substances are present in exhaust gas, the reactor may be easily blocked. Moreover, in order to process a large amount of exhaust gas, it is necessary to enclose several tubular reactors in a bundle or collectively, and thus the size of the processing system is excessively increased. Related prior arts include U.S. Pat. No. 5,236,627, U.S. Pat. No. 5,236,672, U.S. Pat. No. 4,954,320, U.S. Pat. No. 5,843,288, and Korean Patent Publication No: 10-2009-0086761.

Underwater Plasma Discharge

Underwater discharge can be used to remove bacteria and viruses contained in water by forming microbubbles in water and introducing gas having a strong sterilizing power, such as hydroxyl group (OH), active oxygen (O—, $O_2$, $O_3$), and hydrogen peroxide ($H_2O_2$), in water, and its applications include home appliances, such as washing machine, air conditioners, air cleaners, and humidifiers, food processing or catering services, livestock industry, hospital services, etc. which require sterilization/disinfection solutions.

This method of generating active oxygen and ozone bubbles by the underwater discharge is based on a bubble mechanism theory in which a plasma electrode is located in water and a discharge phenomenon occurs in microbubbles generated when water is vaporized by the discharge heat or introduced from the outside, thus generating radicals such as hydroxyl group, active oxygen, hydrogen peroxide, etc. These radicals oxidize heavy metals contained in water and, at the same time, sterilize bacteria and viruses contained in water.

The dielectric barrier electrode is also mainly used as the plasma electrode used in the underwater discharge, like the air cleaning electrode, and this electrode still remains in the above-mentioned plasma electrode structure. Related prior arts include Korean Patent No. 10-0924649 and Korean Patent Publication No. 10-2009-009675.

DISCLOSURE

Technical Problem

Accordingly, the present invention has been made to solve the above-described problems associated with prior art, and an object of the present invention is to provide a dielectric barrier discharge-type plasma generating electrode structure which ensures the stability of plasma, increases the amount of active ions generated, has an excellent sterilizing effect, reduces the amount of ozone generated and the power consumption, and is economic.

Moreover, another object of the present invention is to provide a dielectric barrier discharge-type plasma generating electrode structure which facilitates the formation of a gap between electrodes using a micro gap discharge method and allows a smooth flow of fluid.

Technical Solution

In order to achieve the above objects, the present invention provides an electrode structure comprising:

an upper conductive electrode and a lower conductive electrode;

at least one conductive electrode protrusion formed on at least one inner surface of the upper conductive electrode and the lower conductive electrode facing each other;

a dielectric layer formed with a substantially uniform thickness on at least one inner surface of the upper conductive electrode and the lower conductive electrode facing each other; and a predetermined gap d formed between one of the upper and lower conductive electrodes and the dielectric layer or between the dielectric layers facing each other due to the protrusion effect of the conductive electrode protrusion when the upper conductive electrode and the lower conductive electrode are brought into close contact with each other, wherein a pulse or AC power is applied to the upper conductive electrode and the lower conductive electrode to generate a plasma therebetween.

Moreover, the present invention provides an electrode structure comprising:

an upper conductive electrode, a lower conductive electrode, and an inner conductive electrode;

at least one upper conductive electrode protrusion formed on at least one inner surface of the upper conductive electrode and the inner conductive electrode facing each other;

at least one lower conductive electrode protrusion formed on at least one inner surface of the lower conductive electrode and the inner conductive electrode facing each other;

an upper dielectric layer formed with a substantially uniform thickness on at least one inner surface of the upper conductive electrode and the inner conductive electrode facing each other;

a lower dielectric layer formed with a substantially uniform thickness on at least one inner surface of the lower conductive electrode and the inner conductive electrode facing each other;

a predetermined gap d1 formed between one of the upper and inner conductive electrodes and the upper dielectric layer or between the upper dielectric layers due to the protrusion effect of the upper conductive electrode protrusion when the upper conductive electrode and the inner conductive electrode are brought into close contact with each other; and a predetermined gap d2 formed between one of the lower and inner conductive electrodes and the lower dielectric layer or between the lower dielectric layers due to the protrusion effect of the lower conductive electrode protrusion when the lower conductive electrode and the inner conductive electrode are brought into close contact with each other;

wherein a pulse or AC power is applied to the upper conductive electrode and the lower conductive electrode as one electrode and the inner conductive layer as a counter electrode to generate a plasma discharge between the predetermined gap d1 and the predetermined gap d2 at the same time.

Here, the inner conductive electrode may be separated into two layers, such as an (upper) inner conductive electrode and an (lower) inner conductive electrode, and at least one separated surface conductive electrode protrusion may be formed on at least one of the separated surfaces of the newly formed inner conductive electrodes. Moreover, a dielectric layer may be further formed on at least one of the separated surfaces to form a predetermined gap d3 between the separated surfaces due to the effect of the separated surface conductive electrode protrusion, and thus a plasma may be further generated in the predetermined gap d3 between the separated (upper) inner conductive electrode and (lower) inner conductive electrode by applying a pulse or AC power to the upper conductive electrode and the (lower) inner conductive electrode as one electrode and the lower conductive electrode and the (upper) inner conductive electrode as the other electrode.

Moreover, the pulse or AC power may have a pulse width of 100 is or less and a voltage of 1,000 V or less.

The electrode structure may generate a plasma with a discharge current of 20 mA or less in the predetermined gap d.

The conductive electrode protrusion may be formed with a height of 1,000 μm or less.

The conductive electrode protrusion may have at least one shape selected from the group consisting of a circular shape, a quadrangular shape, a polygonal shape, an oval shape, a star shape, and combinations thereof and may be formed by at least one method selected from the group consisting of press processing, etching processing, welding processing, metal spacer attachment, metal molding processing, and combinations thereof.

At least one of the upper conductive electrode, the lower conductive electrode, and the inner conductive electrode may have a grid shape.

The electrode structure may have a through hole formed in at least one position selected from the group consisting of the upper conductive electrode, the lower conductive electrode, the inner conductive electrode, and the dielectric layer, and the through hole may have at least one shape selected from the group consisting of a circular shape, a quadrangular shape, an oval shape, a polygonal shape, a star shape, other shapes and combinations thereof.

The dielectric layer may be formed by at least one method selected from the group consisting of spraying, plasma spraying, coating, dipping, screen printing, and combinations thereof.

The electrode structure may comprise one or more dielectric layers, and the dielectric layers may be made of the same or different materials.

The electrode structure may further comprise at least one selected from the group consisting of a protective coating layer, another dielectric layer, and a special functional layer (an ozone removal functional layer, an odor removal functional layer, and an insulating layer) which are formed on at least one surface selected from the group consisting of a surface of the upper conductive electrode, a surface of the lower conductive electrode, and a surface of the dielectric layer.

The predetermined gaps d, d1, d2, and d3 may be filled with at least one insulating layer made of at least one selected from the group consisting of ceramic, glass, polymer, and combinations thereof.

Two or more electrode structures may be arranged in series at intervals, insulated and brought into contact with each other, stacked by alternating electrical polarities, or arranged in parallel to each other.

Advantageous Effects

The plasma electrode structure of the present invention having the above-described structure generates less noise, has excellent plasma efficiency, generates many active species, has long lifespan, causes less counter-pressure of air, has excellent power consumption, and ensures removal of air conditioner odor as well as air cleaning and sterilization.

Moreover, it is possible to configure the plasma electrode structure in various manners depending on the characteristics required for each application, which makes it possible to overcome most limitations in electrode design due to the existing plasma electrode structures, and thus the plasma electrode structure of the present invention is significantly advantageous for miniaturization.

Accordingly, the electrode structure of the present invention can be easily applied to other gaseous fluids and liquid such as water without being limited to the air cleaning field, and in the case of water, microbubbles in water are ionized by plasma, which makes it possible to sterilize and clean water by the same principle as the air cleaning. Thus, the electrode structure of the present invention can be easily applied to various applications other than the air cleaning.

BEST MODE FOR CARRYING OUT THE INVENTION

Hereinafter, the present invention will be described in detail.

Figure 1:
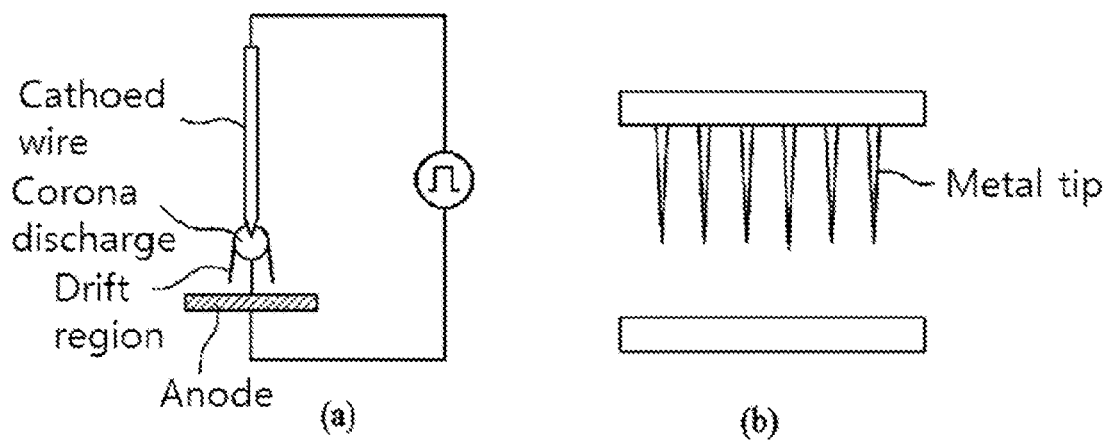
FIG. 1 shows a typical structure of a corona discharge electrode.
Figure 2:
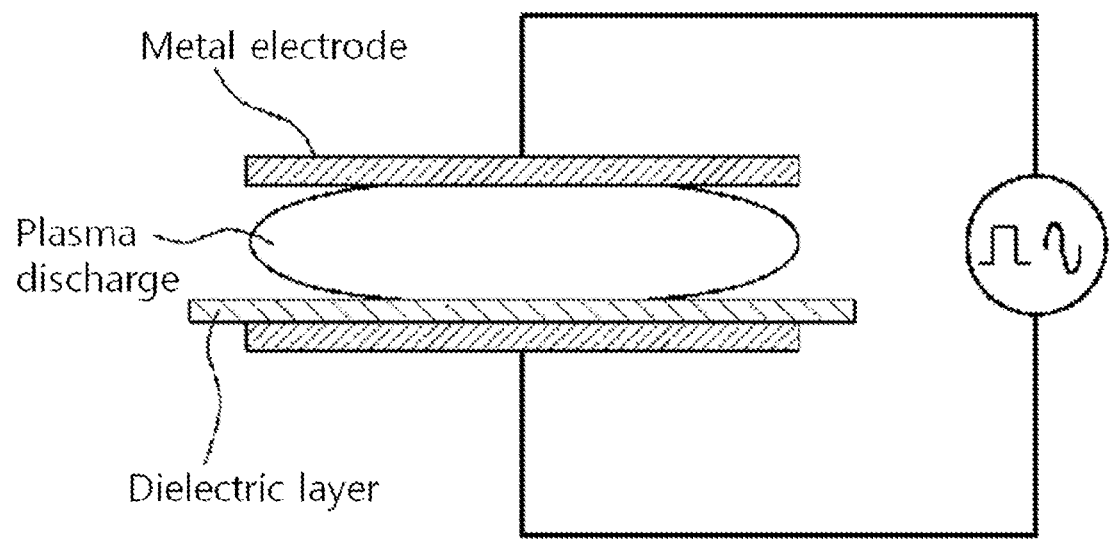
FIG. 2 shows a typical structure of a dielectric barrier plasma electrode.
Figure 3:
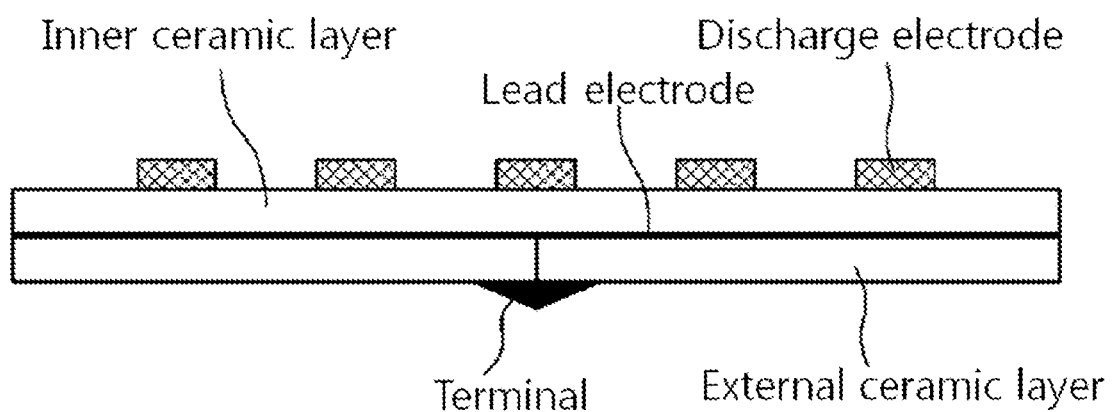
FIG. 3 shows a typical structure of a surface discharge electrode.
Figure 4:
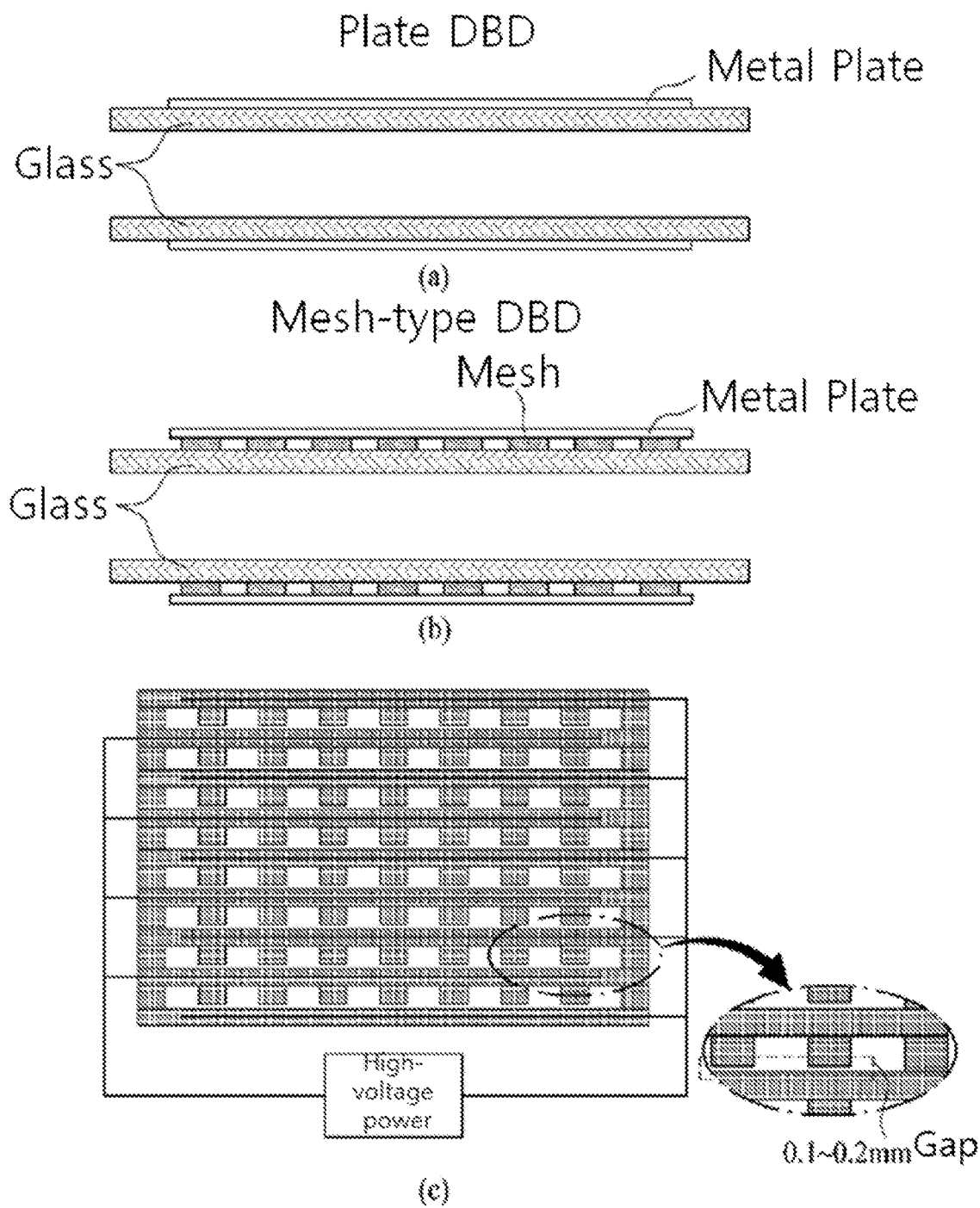
FIG. 4 shows a typical structure of a silent discharge (Volume DBD) electrode, in which (a) shows a plate-type DBD, (b) shows a mesh-type DBD, and (c) shows a micro gap DBD.
Figure 5:
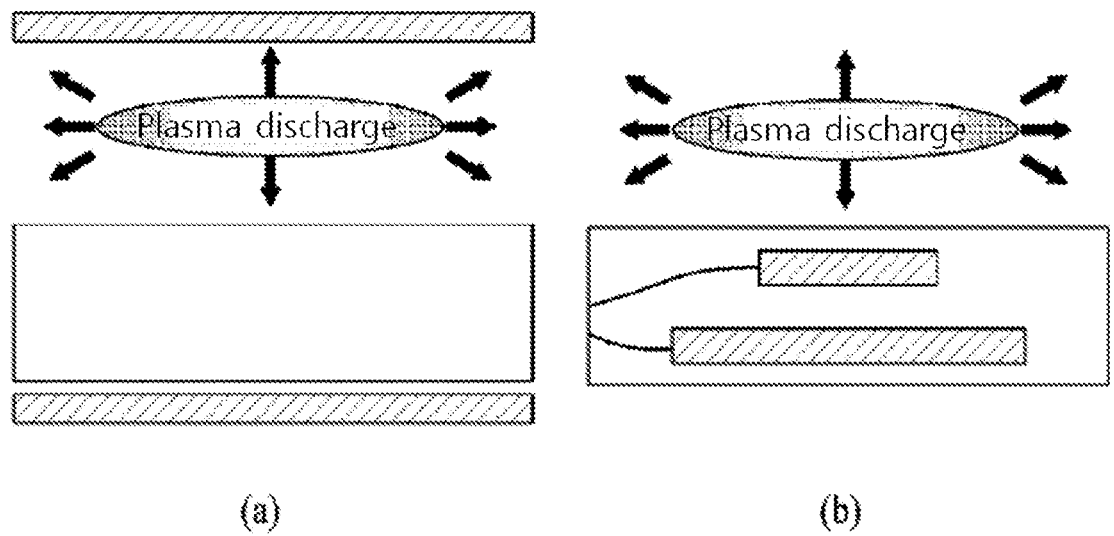
FIG. 5 shows a plasma generation region in a typical structure of a volume dielectric barrier discharge (volume DBD) electrode.

Up to now, there are various electrode barrier plasma electrodes, but as shown in FIGS. 5(a) and (b), they all have something in common in that an electrode and a dielectric layer are formed in a plate shape and arranged in parallel, in which the plasma generation occurs in parallel to the electrode array and the flow of fluid also occurs in parallel to the electrode array. Cylindrical plate structures are present in some electrodes, but the results are the same as the plate-type structure. Even in the case of the micro gap method, a complicated design is required to maintain the micro gap between the electrodes, a counter-pressure against the flow of the fluid is caused due to a reduced fluid passage gap, the noise is increased, and thus the through hole is occasionally used to solve these problems.

Due to these structure limitations, the existing electrode structures have a fundamental limitation in electrode design that cannot easily meet the characteristics required for each application. Accordingly, in order to overcome this limitation, the present invention suggests an electrode structure which facilitates the formation and maintenance of a gap between electrodes by employing a micro gap method having excellent efficiency, in which a protrusion (embossing or metal etching) is directly formed on a plate-type metal electrode as a conductor, a dielectric layer is formed with a uniform thickness thereon, and then a pair of electrodes are brought into close contact with each other so as to maintain the gap between the electrodes, which is the core of the micro gap method, and to facilitate the control of the height of the gap economically and simply.

This structure may appear to be a simple invention, but it is an invention that requires special considerations on the problem of electricity leakage due to direct contact between the conductor and the dielectric, the method of forming the dielectric layer with a uniform thickness on the metal electrode having the protrusion, the problem of insulation breakdown due to the protrusion of the conductor, and the problem of impact fracture of the protrusion due to the close contact between the electrodes. Moreover, this method has not been attempted until now and does not require any further process to form the gap.

Figure 6:
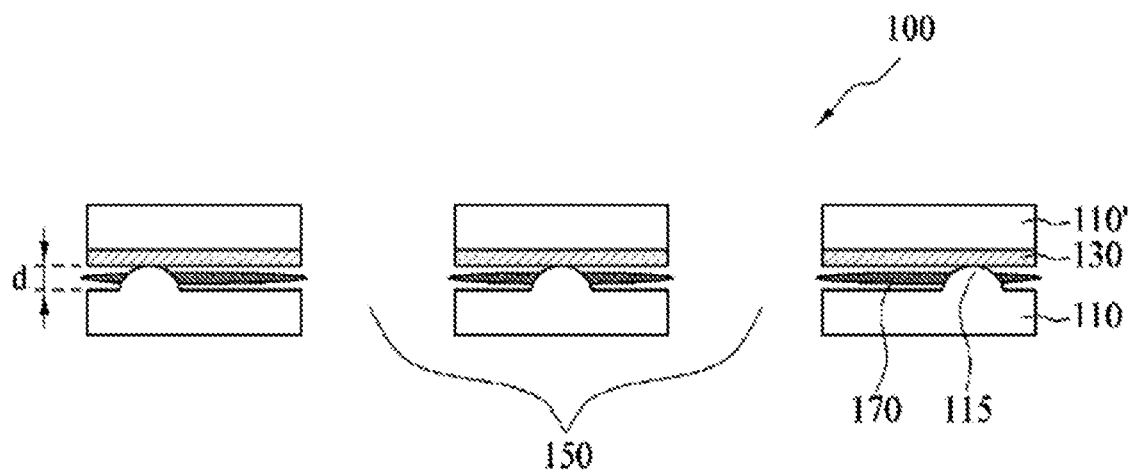
FIG. 6 shows a plasma dielectric barrier electrode structure and a plasma generation area in accordance with an embodiment of the present invention.

FIG. 6 shows a plasma dielectric barrier electrode structure and a plasma generation area in accordance with an embodiment of the present invention.

As shown in FIG. 6, a dielectric barrier plasma electrode structure 100 of the present invention comprises: an upper conductive electrode 110' and a lower conductive electrode 110; at least one conductive electrode protrusion 115 formed on at least one inner surface of the upper conductive electrode 110' and the lower conductive electrode 110 facing each other; and a dielectric layer 130 formed with a substantially uniform thickness on at least one inner surface of the upper conductive electrode 110' and the lower conductive electrode 110 facing each other.

Moreover, the electrode structure 100 of the present invention comprises a predetermined gap d formed between one of the upper and lower conductive electrodes 110' and 110 and the opposite dielectric layer 130 or between the dielectric layers 130 due to the protrusion effect of the conductive electrode protrusion 115 when the upper conductive electrode 110' and the lower conductive electrode 110 are brought into close contact with each other. Moreover, a plasma discharge 170 is generated in the predetermined gap d by applying a pulse or AC power to the upper conductive electrode 110' and the lower conductive electrode 110, and then fluid active species produced by the plasma are supplied to a fluid flowing therein, thereby cleaning the fluid.

The power applied to the upper conductive electrode 110' and the lower conductive electrode 110 may have a pulse width of 100 μs or less and a voltage of 1,000 V or less, and the current of the plasma discharge may be 20 mA or less.

In the present invention, the electrode protrusion 115 plays an important role in forming the predetermined gap d. Specifically, when the upper conductive electrode 110' and the lower conductive electrode 110 are brought into close contact with each other, the electrode protrusion 115 acts as a spacer that forms a predetermined gap d between one of the upper and lower conductive electrodes 110' and 110 and the opposite dielectric layer 130 or between the dielectric layers 130 due to the protrusion effect of the conductive electrode protrusion 115. In other words, due to the effect of the conductive electrode protrusion 115, the predetermined gap d is formed between the upper conductive electrode 110' and the dielectric layer 130 formed on the lower conductive electrode 110, between the lower conductive electrode 110 and the dielectric layer 130 formed on the upper conductive electrode 110', or between the dielectric layer 130 formed on the upper conductive electrode 110' and the dielectric layer 130 formed on the lower conductive electrode 110 such that the plasma 170 can be effectively formed in the gap d.

Here, the height of the conductive electrode protrusion 115 is in the range of 1,000 μm or less which is used in the micro gap method, and the number of electrode protrusions 115 may be freely adjusted within the range in which the gap between the electrodes is maintained.

The electrode protrusion 115 may be formed on either or both of the upper conductive electrode 110' and the lower conductive electrode 110. Moreover, the gap between the upper conductive electrode 110' and the lower conductive electrode 110 may vary depending on the position by varying the height of the conductive electrode protrusion 115 depending on the position.

In the electrode structure of the micro gap method, an external structural support has been used or a ceramic insulator has been inserted between the electrodes to maintain the gap between the electrodes. However, in the case of the micro gap method, the gap between the electrodes is in units of micrometers (m), and thus it is extremely difficult to maintain the micro gap using the external structural support. Moreover, in order to maintain the micro gap using a ceramic insulator, it is necessary to make a prototype of a micro pattern for the formation of an insulating ceramic spacer on the dielectric layer and then form an insulating ceramic spacer again according to the micro pattern, which thus complicates the process and significantly increases the production cost as there are great difficulties in precisely controlling the height of the spacer.

The conductive electrode protrusion is a conductor, and when the conductive electrode protrusion and the dielectric layer are structurally brought into contact with each other, the electric charges accumulated on the surface of the dielectric layer rapidly migrate to the conductive electrode, resulting in current leakage that causes loss of electricity. Moreover, due to the structural protrusion, there are various problems such as the occurrence of cracks and insulation breakdown, etc., and thus this method has not yet been attempted. However, in the present invention, with the use of the conductive protrusion, it has been possible to effectively realize the function of the plasma electrode by minimizing the contact area between the conductor and the dielectric layer, uniformly controlling the thickness of the dielectric layer, and controlling the pressure during contact between the electrodes.

Moreover, in the present invention, the conductive electrode protrusion 115 may have at least one shape selected from the group consisting of a circular shape, a quadrangular shape, an oval shape, a polygonal shape, a star shape, and combinations thereof.

Furthermore, the conductive electrode protrusion 115 is formed by pressing a conductive electrode substrate to a predetermined height by a method such as press processing or by attaching other metals to the conductive electrode substrate. Specifically, the conductive electrode protrusion 115 may be formed by at least one method selected from the group consisting of press processing, etching processing, welding processing, metal spacer attachment, metal molding processing, and combinations thereof.

Meanwhile, in the present invention, the upper conductive electrode 110' and the lower conductive electrode 110 may generally be a flat plate having a circular shape, a quadrangular shape, an oval shape, or other shapes, but a concave or convex shape may be possible depending on the required characteristics. Moreover, at least one of the upper conductive electrode 110' and the lower conductive electrode 110 may have a grid or mesh shape to enhance its function.

Further, the dielectric barrier electrode structure 100 of the present invention may have a through hole 150 formed in at least one position selected from the group consisting of the upper conductive electrode 110', the lower conductive electrode 110, and the dielectric layer 130. That is, one or more through holes are formed in the plate-type electrode structure such that a fluid flows through the through holes. The application of the through holes is a technique that is widely used to reduce the counter-pressure against the flow of the fluid.

Figure 10:
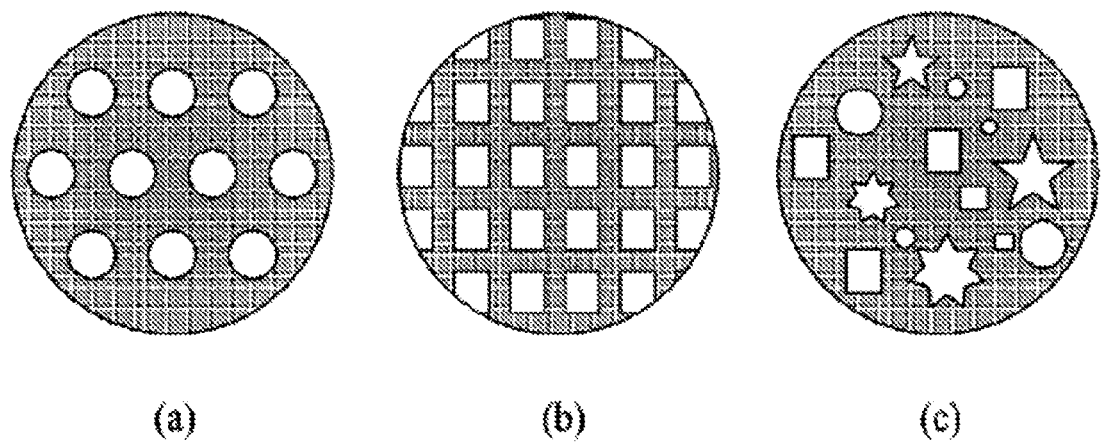
FIG. 10 shows various types of through hole patterns of a plasma electrode in accordance with an embodiment of the present invention.

Here, as shown in FIG. 10, the through hole 150 may have at least one shape selected from the group consisting of a circular shape, a quadrangular shape, an oval shape, a polygonal shape, a star shape, other shapes and combinations thereof, and the pattern of the through holes 150 may be varied by combining the size and/or the shape of the holes.

Moreover, the dielectric layer 130 may be basically made of ceramic, quartz, or glass which has electrical insulation and dielectric properties at the same time, its thickness may be in the range of several micrometers (μm) to several millimeters (mm), and its area may be arbitrarily set depending on the processing capacity, for example, in the range of several square millimeters ($mm^2$) to hundreds of square centimeters ($cm^2$). The dielectric layer 130 may be formed by at least one method selected from the group consisting of spraying, plasma spraying, coating, dipping, screen printing, bonding, and combinations thereof.

Furthermore, the dielectric layer 130 may be made of a mixture of two or more dielectric compositions and may be formed as one or more layers. When one or more dielectric layers are formed, the dielectric layers may be made of the same or different materials.

In addition, the properties of the plasma generated may be varied by varying the number of dielectric layers 130, the total thickness, and the material, and the dielectric layers may be made of different materials for each layer to enhance the electrode characteristics.

Moreover, the electrode structure 100 of the present invention may further comprise at least one layer selected from the group consisting of a protective coating layer, another dielectric layer, an ozone removal functional layer, an odor removal functional layer, and an insulating layer, which are formed on at least one surface selected from the group consisting of a surface of the upper conductive electrode 110', a surface of the lower conductive electrode 110, and a surface of the dielectric layer 130, thus enhancing the function. With the application of this method, various complex functions can be realized in a miniaturized plasma electrode.

Figure 11:
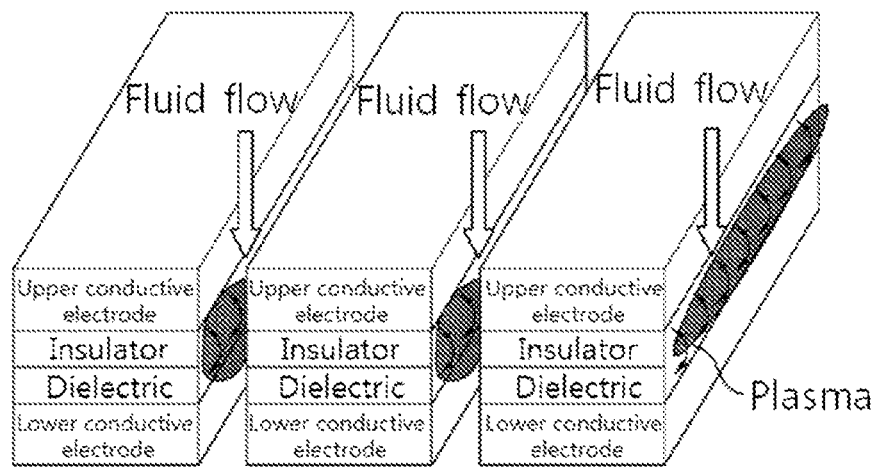
FIG. 11 shows a plasma electrode structure and a plasma generation area in accordance with still yet another embodiment of the present invention.
Figure 11:
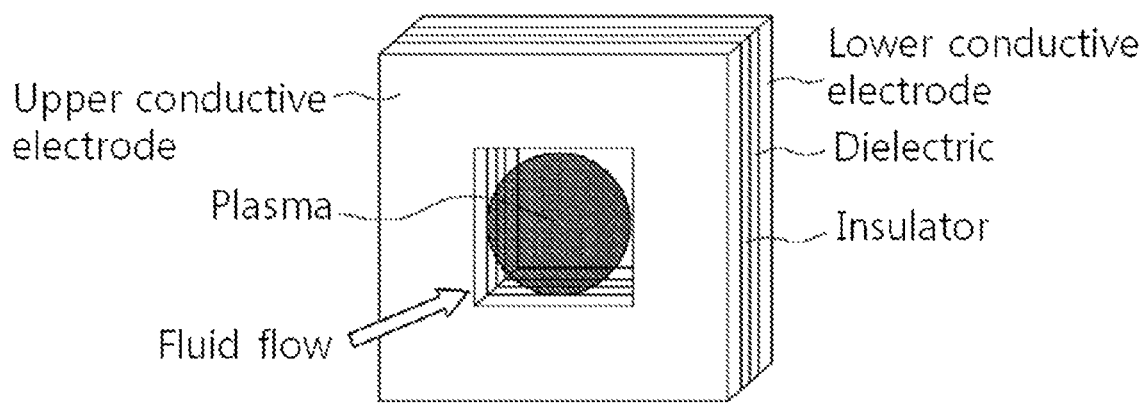

Furthermore, in the present invention, the predetermined gap d may be filled with an insulator, made of ceramic, glass, or polymer, other than a fluid in a space where the fluid (air, water, etc.) moves, if necessary. When the predetermined gap d is filled with such an insulator and when the conductive electrode has the through hole or the grid shape, the plasma is generated on the side of the through hole and the side cross section of the grid, respectively, which may also be a very effective method of generating the plasma. An embodiment of this case is shown in FIG. 11.

Figure 7:
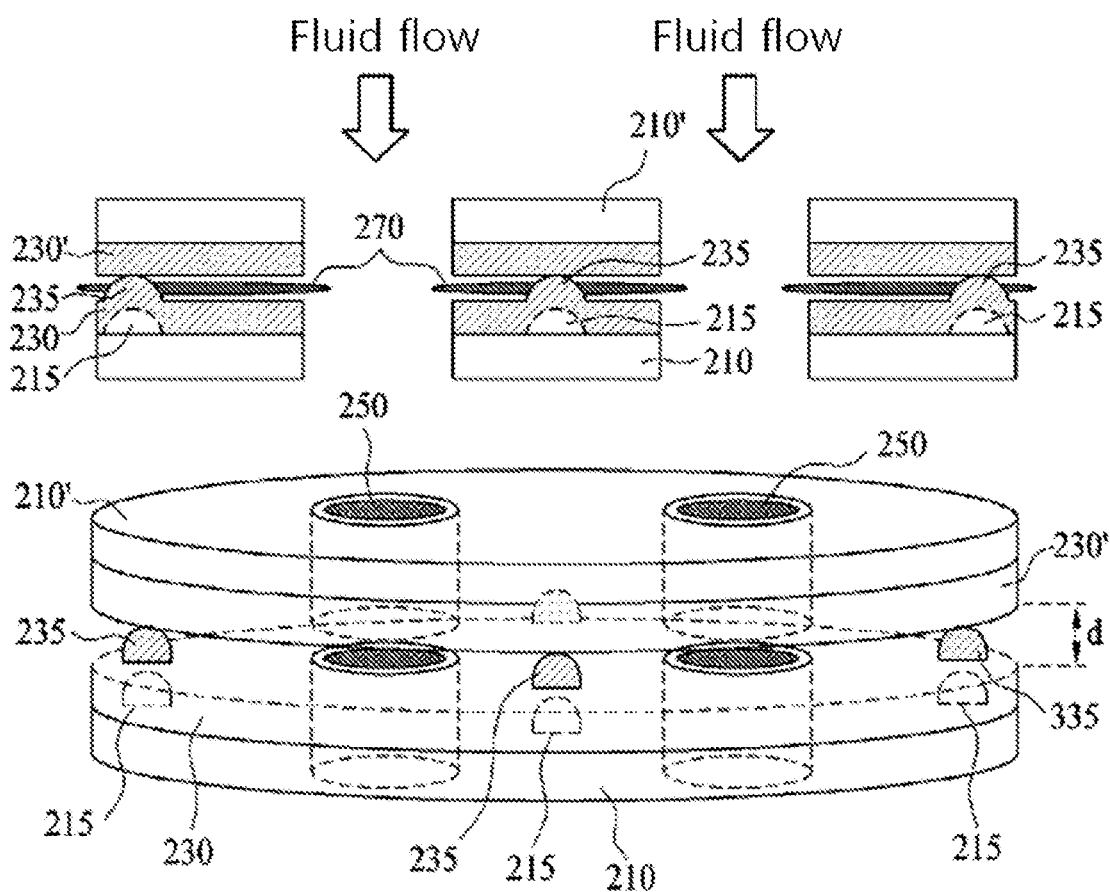
FIG. 7 shows a plasma dielectric barrier electrode structure and a plasma generation area in accordance with another embodiment of the present invention.

FIG. 7 shows a plasma dielectric barrier electrode structure and a plasma generation area in accordance with another embodiment of the present invention.

The embodiment shown in FIG. 7 is different from that shown in FIG. 6 in that a dielectric layer is formed with a uniform thickness on the protrusion of the conductive electrode, and as a result, a predetermined gap d is formed between an upper dielectric layer 230' and a lower dielectric layer 230. Moreover, FIG. 7 shows an electrode structure in three-dimensions where through holes are introduced.

In this case, there is no direct contact between the conductive electrode and the dielectric layer, and a dielectric layer protrusion 235 is formed corresponding to the formation of an electrode protrusion 215 to maintain a gap d between the dielectric layers. The material of the dielectric layer protrusion 235 is the same as the dielectric layers 230 and 230'.

Any one of the dielectric layers 230 and 230' may be omitted, and in particular when the dielectric layer 230 is omitted, this structure is the same as FIG. 6. The dielectric layers 230 and 230' should have a thickness enough to endure the applied voltage, and the thickness may vary depending on the material.

Figure 8:
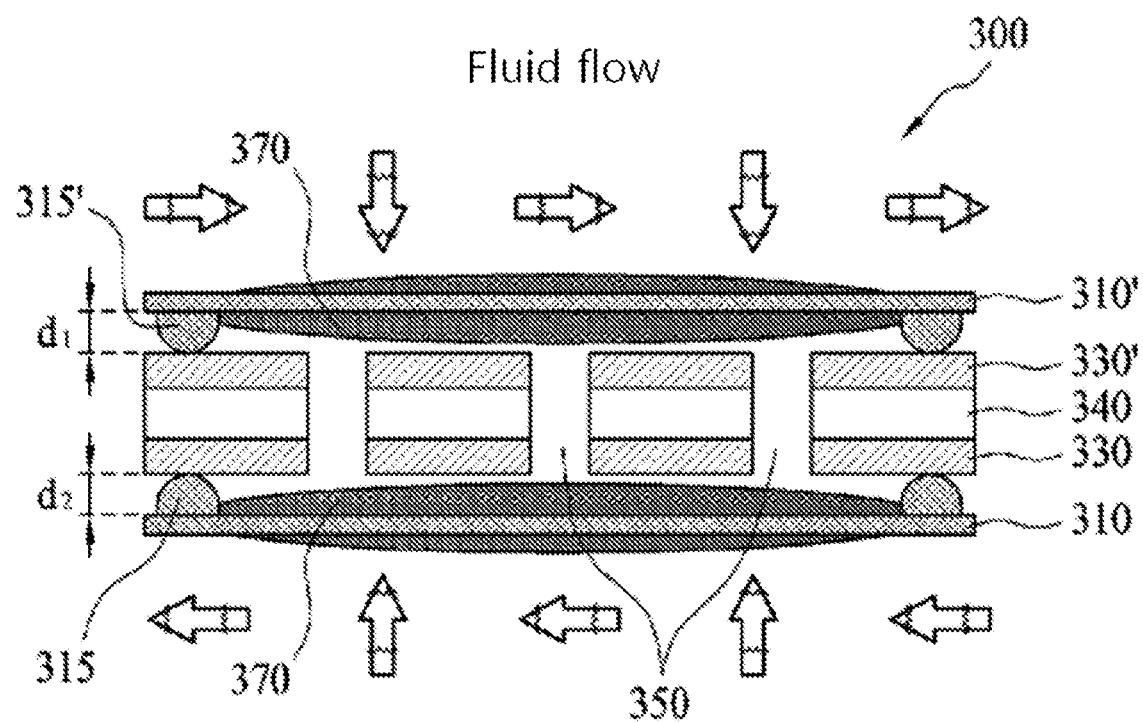
FIG. 8 shows a plasma dielectric barrier electrode structure and a plasma generation area in accordance with still another embodiment of the present invention.

Meanwhile, FIG. 8 shows a plasma dielectric barrier electrode structure and a plasma generation area in accordance with still another embodiment of the present invention.

As shown in FIG. 8, an electrode structure 300 of the present invention comprises an upper conductive electrode 310', a lower conductive electrode 310, and an inner conductive electrode 340.

Moreover, the electrode structure 300 of the present invention comprises: at least one upper conductive electrode protrusion 315' formed at least one surface of the upper conductive electrode 310' and the inner conductive electrode 340 facing each other; and at least one lower conductive electrode protrusion 315 formed at least one surface of the lower conductive electrode 310 and the inner conductive electrode 340 facing each other.

Furthermore, the electrode structure 300 of the present invention comprises: an upper dielectric layer 330' formed with a substantially uniform thickness on at least one inner surface of the upper conductive electrode 310' and the inner conductive electrode 340 facing each other; and a lower dielectric layer 330 formed with a substantially uniform thickness on at least one inner surface of the lower conductive electrode 310 and the inner conductive electrode 340 facing each other.

In addition, the electrode structure 300 of the present invention comprises a predetermined gap d1 formed between one of the upper and lower conductive electrodes and the upper dielectric layer 330' or between the upper dielectric layers 330' due to the protrusion effect of the upper conductive electrode protrusion 315' when the upper conductive electrode 310' and the inner conductive electrode 340 are brought into close contact with each other. In other words, due to the effect of the upper conductive electrode protrusion 315', the predetermined gap d1 may be formed between the upper conductive electrode 310' and the upper dielectric layer 330' formed on the inner conductive electrode 340, between the inner conductive electrode 340 and an upper dielectric layer (not shown) formed on the upper conductive electrode 310', or between a dielectric layer (not shown) formed on the upper conductive electrode 310' and the dielectric layer 330' formed on the inner conductive electrode 340.

Moreover, the electrode structure 300 of the present invention comprises a predetermined gap d2 formed between one of the lower and inner dielectric layers and the lower dielectric layer 330 or between the lower dielectric layers 330 due to the protrusion effect of the lower conductive electrode protrusion 315 when the lower conductive electrode 310 and the inner conductive electrode 340 are brought into close contact with each other. That is, due to the effect of the lower conductive electrode protrusion 315, the predetermined gap d2 may be formed between the lower conductive electrode 310 and the lower dielectric layer 330 formed on the inner conductive electrode 340, between the inner conductive electrode 340 and a lower dielectric layer (not shown) formed on the lower conductive electrode 310, or between a lower dielectric layer (not shown) formed on the lower conductive electrode 310 and the lower dielectric layer 330 formed on the inner conductive electrode 340.

Here, a pulse or AC power is applied to the upper conductive electrode 310' and the lower conductive electrode 310 as one electrode and the inner conductive layer 340 as a counter electrode to generate a plasma discharge 370 between the predetermined gap d1 of the upper electrodes and the predetermined gap d2 of the lower electrodes, and then fluid active species produced by the plasma are supplied to a fluid flowing therein, thereby cleaning the fluid.

Moreover, in the present embodiment, the upper and lower conductive electrodes 310' and 310 may be grid-type conductive electrodes, and the inner conductive electrode may have a through hole shape as shown in FIG. 8. In this case, as shown in FIG. 8, the plasma is generated in an open space, and thus the flow of the fluid can be distributed in all directions regardless of the direction of the plate-type electrode shape, thereby significantly improving the resistance to the flow of the fluid. Furthermore, the plasma 370 is generated on both the top and bottom of the structure 300, and the efficiency is doubled.

The electrode structure 300 in the present embodiment is significantly different from the electrode structures 100 and 200 described with reference to FIGS. 6 and 7 in that the electrode structure 300 comprises the inner conductive layer 340 between the upper conductive layer 310' and the lower conductive layer 310. Moreover, the upper and lower conductive electrodes 310' and 310 and the inner conductive layer 300 having the dielectric layers 330 and 330' are spaced a predetermined gap d, which is caused by the presence of the electrode protrusions 315 and 315' formed on the inner surfaces of the conductive electrodes 310 and 310', providing unique characteristics that allow the conductive electrode protrusions to be brought into direct contact with the dielectric layers.

In the present invention, the pulse or AC power may have a pulse width of 100 is or less and a voltage of 1,000 V or less, and the current of the plasma discharge may be 20 mA or less.

Moreover, in the present invention, the conductive electrode protrusions 315 and 315' act as a spacer that forms the gaps d1 and d2, and the gaps d1 and d2 may have the same or different sizes.

Here, the height of the conductive electrode protrusions 315 and 315' is in the range of 1,000 μm or less which is used in the micro gap method, and the number of conductive electrode protrusions 315 and 315' may be freely adjusted within the range in which the gap between the electrodes is maintained. The conductive electrode protrusions 315 and 315' may be formed on at least one surface of the upper conductive electrode, the lower conductive electrode, and the inner conductive electrode. Moreover, the gap between the upper conductive electrode and the lower conductive electrode may vary depending on the position by varying the height of the conductive electrode protrusion depending on the position.

Furthermore, in the present invention, the conductive electrode protrusions 315 and 315' may have at least one shape selected from the group consisting of a circular shape, a quadrangular shape, an oval shape, a polygonal shape, a star shape, and combinations thereof.

In addition, the conductive electrode protrusions 315 and 315' are formed by pressing a conductive electrode substrate to a predetermined height by a method such as press processing or by attaching other metals to the conductive electrode substrate. Specifically, the conductive electrode protrusions 315 and 315' may be formed by at least one method selected from the group consisting of press processing, etching processing, welding processing, metal spacer attachment, metal molding processing, and combinations thereof.

Meanwhile, in the present invention, the upper conductive electrode 310', the lower conductive electrode 310, and the inner conductive electrode 340 may generally be a flat plate having a circular shape, a quadrangular shape, an oval shape, or other shapes, but a concave or convex shape may be possible depending on the required characteristics. Moreover, at least one of the upper conductive electrode 310', the lower conductive electrode 310, and the inner conductive electrode 340 may have a grid or mesh shape to enhance its function.

Further, the dielectric barrier electrode structure 300 of the present invention may have a through hole 350 formed in at least one position selected from the group consisting of the upper conductive electrode 310', the lower conductive electrode 310, the inner conductive electrode 340, and the dielectric layers 330 and 330'. That is, one or more through holes are formed in the plate-type electrode structure such that a fluid flows through the through holes. The application of the through holes is a technique that is widely used to reduce the counter-pressure against the flow of the fluid.

Here, as shown in FIG. 10, the through holes 350 may have at least one shape selected from the group consisting of a circular shape, a quadrangular shape, an oval shape, a polygonal shape, a star shape, other shapes and combinations thereof, and the pattern of the through holes 350 may be varied by combining the size and/or the shape of the holes.

Moreover, the dielectric layers 330 and 330' may be basically made of ceramic, quartz, or glass which has electrical insulation and dielectric properties at the same time, its thickness may be in the range of several micrometers to several millimeters (mm), and its area may be arbitrarily set depending on the processing capacity, for example, in the range of several square millimeters ($mm^2$) to hundreds of square centimeters ($cm^2$). The dielectric layers 330 and 330' may be formed by at least one method selected from the group consisting of spraying, plasma spraying, coating, dipping, screen printing, bonding, and combinations thereof.

Furthermore, the dielectric layers 330 and 330' may be made of a mixture of two or more dielectric compositions and may be formed as one or more layers. When one or more dielectric layers are formed, the dielectric layers may be made of the same or different materials.

In addition, the properties of the plasma generated may be varied by varying the number of dielectric layers, the total thickness, and the material, and the dielectric layers may be made of different materials for each layer to enhance the electrode characteristics.

Moreover, the electrode structure 300 of the present invention may further comprise at least one layer selected from the group consisting of a protective coating layer, another dielectric layer, and a special functional layer (an ozone removal functional layer, an odor removal functional layer, and an insulating layer), which are formed on at least one surface selected from the group consisting of a surface of the upper conductive electrode, a surface of the lower conductive electrode, a surface of the inner conductive electrode, and a surface of the dielectric layer, thus enhancing the function. With the application of this method, various complex functions can be realized in a miniaturized plasma electrode.

Furthermore, in the present invention, the predetermined gaps d1 and d2 may be filled with an insulator, made of ceramic, glass, or polymer, other than a fluid in a space where the fluid (air, water, etc.) moves, if necessary. When the predetermined gaps d1 and d2 are filled with such an insulator and when the conductive electrode has the through hole or the grid shape, the plasma is generated on the side of the through hole and the side cross section of the grid, respectively, which may also be a very effective method of generating the plasma. An embodiment of this case is shown in FIG. 11.

Figure 9:
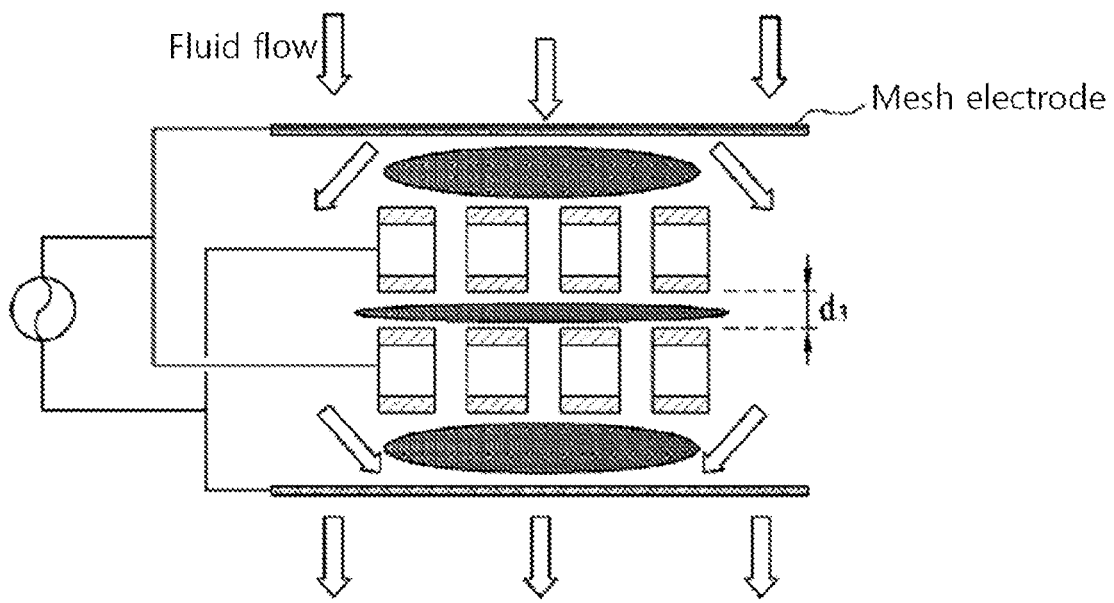
FIG. 9 shows a plasma dielectric barrier electrode structure and a plasma generation area in accordance with yet another embodiment of the present invention.

Meanwhile, FIG. 9 shows an alternative of the embodiment of FIG. 8. In this case, the inner conductive electrode 340 of FIG. 9 is separated into two layers, such as an (upper) inner conductive electrode and an (lower) inner conductive electrode, at least one separated surface conductive electrode protrusion is formed on at least one of the separated surfaces of the newly formed inner conductive electrodes, and a dielectric layer is further formed on at least one of the separated surfaces.

Here, when the separated inner conductive electrodes are brought into close contact with each other, a predetermined gap d3 is formed on the separated surfaces due to the effect of the separate surface conductive electrode protrusions on the separated surfaces of the inner conductive electrodes. Therefore, the plasma is additionally generated in the predetermined gap d3 between the separated surfaces of the inner conductive electrodes by configuring the upper conductive electrode and the (lower) inner conductive electrode as one electrode and configuring the lower conductive electrode and the (upper) inner conductive electrode as the other electrode. As a result, as shown in FIG. 9, the plasma is generated in three places such as the top, middle, and bottom of the electrodes, thereby further increasing the plasma efficiency.

Although the conductive electrode protrusion is shown in FIG. 9, the structure and the formation method thereof are the same as described above. Moreover, the application and description of the through holes, the method of forming the dielectric layer, and the grid-shaped conductive electrodes described in FIGS. 7, 8, and 9 apply to the present embodiment in the same manner.

Figure 12:
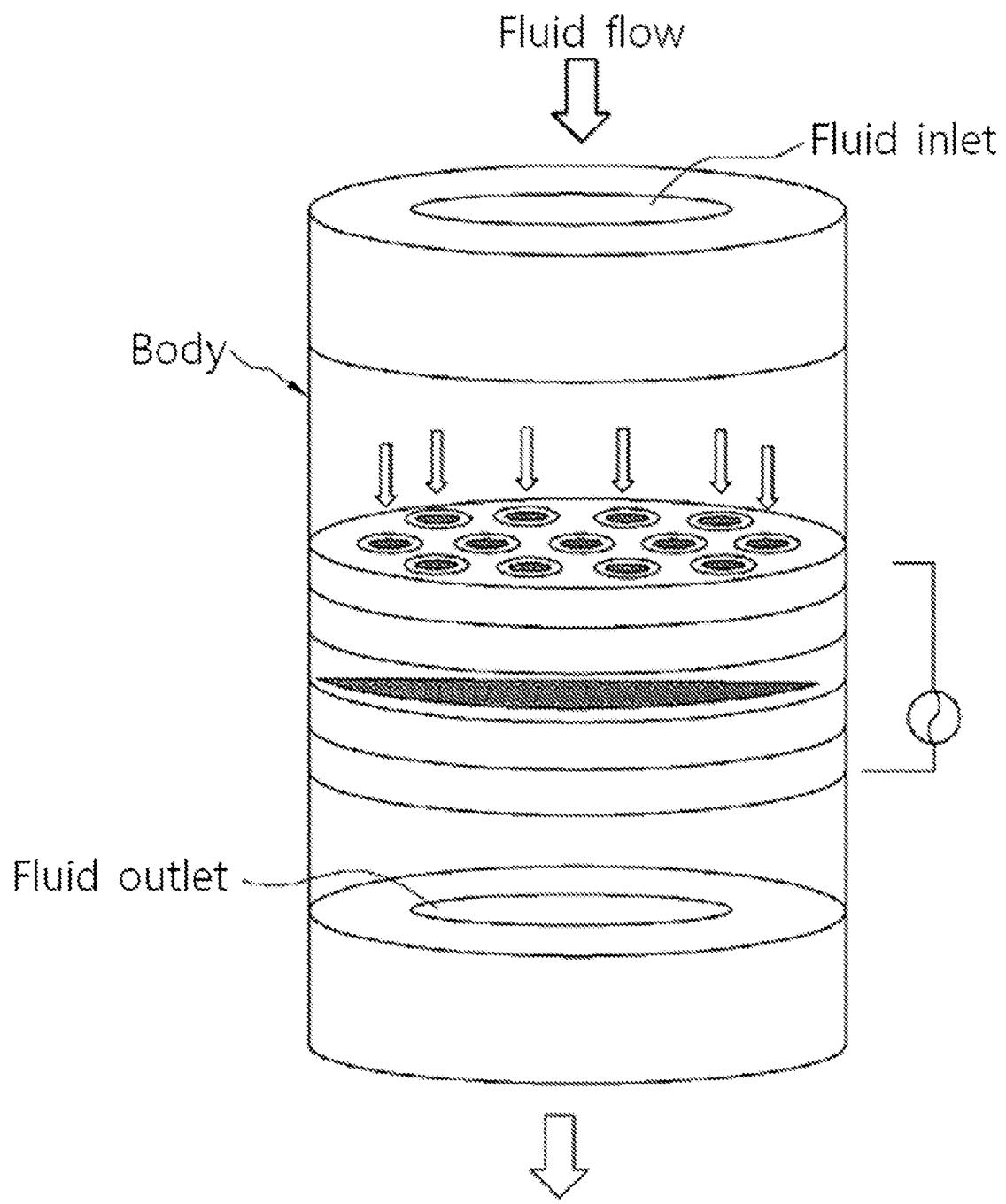
FIG. 12 shows a fluid cleaning reactor in accordance with an embodiment of the present invention.

FIG. 12 shows a fluid cleaning reactor in accordance with an embodiment of the present invention.

As shown in FIG. 12, a fluid cleaning reactor using a low-temperature plasma according to the present invention comprises a body that is at least greater than the area of the plasma electrode. A flow distributor provided with an inlet for introducing a fluid into the body is installed in front of the body. The body comprises one or more plasma electrode structures. Moreover, an outlet through which the fluid passing through the electrodes can be discharged is provided at the rear of the electrode structure.

As shown in FIG. 12, the complete plasma electrode structure is arranged perpendicular to the flow of the fluid in the reactor body, and the contact region other than electrical terminals is insulated. According to a reaction process of the reactor configured as above, when a power is applied to the reactor by operating a power supply, an electric discharge is generated in a predetermined gap between an upper electrode and a lower electrode to generate plasma.

By the action of ultraviolet rays, electrons, ions and radicals such as active oxygen, ozone, OH, etc. generated by the plasma, harmful gases in a fluid passing through a through hole of the electrode structure are changed into harmless substances, and this reaction is a principle that uses the typical low-temperature plasma.

Even in the case where a stacking structure, which is being used in the battery field, is employed in the electrode structure of the present invention such that the electrodes are stacked in an alternating manner, the principle of the present invention may also be applied as it is.

Figure 13:
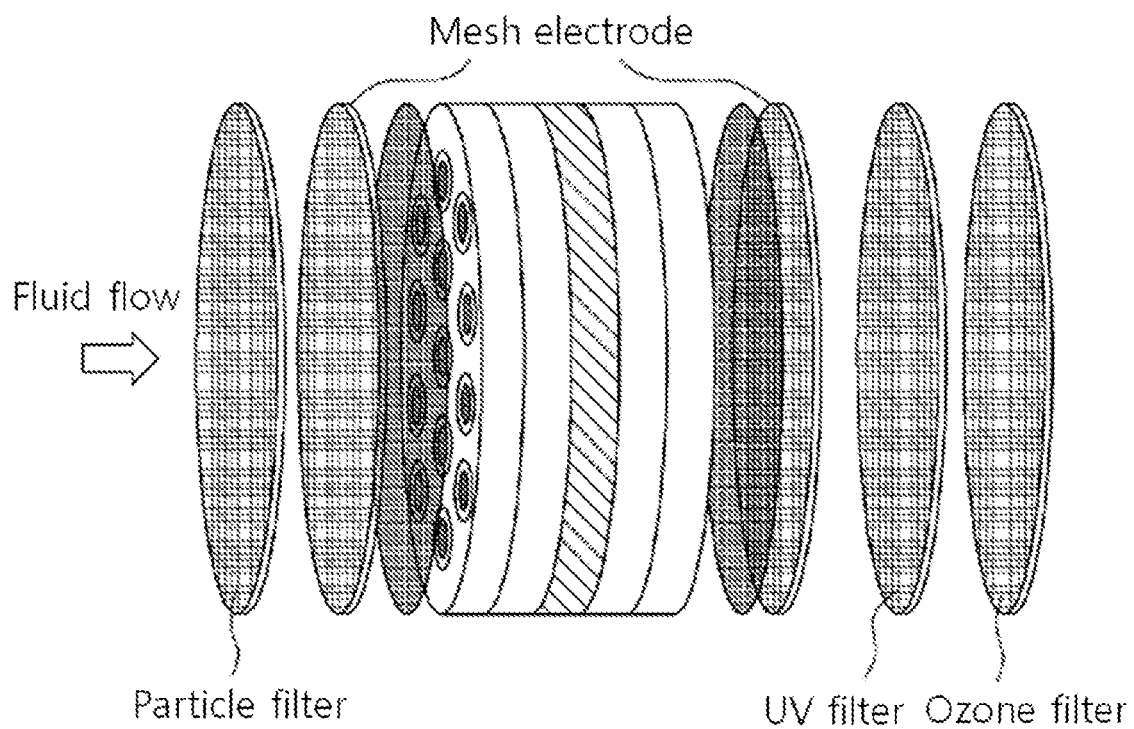
FIG. 13 shows an exemplary configuration of a plasma DBD electrode in accordance with an embodiment of the present invention.

Due to the nature of the electrode structure of the present invention, it is easy to arrange various filters or mesh screens in series in the front and rear of the electrode structure, and thus it is possible to apply additional filters or screens that complement the ozone removal function, the ultraviolet enhancement function, and the odor removal function. That is, as shown in FIG. 13, a particle filter, an ultraviolet enhancement filter, and an ozone filter may be arranged together in the front and rear of the electrode structure.

Moreover, two or more electrode structures of the present invention may be arranged in series at intervals, insulated and brought into contact with each other, or stacked by alternating electrical polarities, and may be arranged in parallel to increase the processing capacity.

In the present invention, the fluid may be a gas such as air or a liquid such as water, and when the electrode structure is located in water, it is possible to easily and effectively generate a discharge in water, and thus this electrode structure can be applied to various fields other than the air cleaning field.

The above-described electrode structure of the present invention may appear to be a relatively simple invention on one side, but can be obtained only when there are significant considerations on the plasma generation principle and the characteristics required for each application, and its advantages are as follows.

First, the method of forming the gap between the electrodes may appear to be a simple invention, but in this case, the conductive electrode protrusion and the dielectric layer are structurally brought into contact with each other to cause electrical leakage and arc, and thus this method has not been attempted until now. That is, it is necessary to design the contact area between the structural protrusion and the dielectric layer based on technical understanding of the plasma electrode structure, to uniformly form the dielectric layer over the protrusion, and to design the thickness of the dielectric layer by considering the electrical properties of the material for the dielectric layer, thus preventing the generation of the arc.

Second, when the shape of the through hole and the shape of the grid of the electrode structure are changed, a change in electric field is induced, which makes it possible to provide various properties to the plasma electrode. That is, when a pointed shape is formed in the cross section of the through hole, electrons are focused on this area, which facilitates the generation of the plasma, thereby easily generating the plasma at low voltage. In the case of a circular shape, the electric field is uniformly distributed to reduce the voltage concentration, which prevents the streamer discharge, thereby creating a uniform glow discharge. As a result, it is possible to easily design the plasma discharge. When the pattern and size of the through hole are mixed, it is possible to control the ratio of the streamer discharge to the glow discharge, the amount of active ions generated, the amount of ultraviolet rays produced, the discharge inception voltage, and the power consumption.

MODE FOR INVENTION

Next, the present will be described in detail with respect to the following Examples Example 1

In order to evaluate the performance of a plasma electrode structure, an air cleaning module comprising a fluid inlet, a plasma electrode, and a fluid outlet was used. An electrical electrode was made of stainless steel 403 with a circular plate shape having a diameter of 50 mm and a thickness of 1 mm. Then, five electrode protrusions were formed on the outer periphery of the diameter of the plate at a uniform angle and a height of 50 µm using a press, and five protrusions were formed in the center of the radius in the same manner. Moreover, forty eight circular through holes having a diameter of 3.6 mm were uniformly distributed on the plate. The opening area corresponds to 25% of the whole area. Then, a dielectric layer was formed with a thickness of 70 µm on a circular metal plate by a typical spraying process using alumina and barium titanate powders having a particle size of 1-2 um as a dielectric composition and polyvinylidene fluoride (PVDF) as a binder, and another circular plate having the same structure was prepared. These two circular plates were brought into close contact with each other to face the dielectric layer, thus completing the electrode structure.

Subsequently, an AC power with a voltage of 1,000 V and a frequency of 700 kHz was applied to the electrode structure, and the number of anions generated and the concentration of ozone generated were measured at an air outlet using an ion counter and an ozone analyzer. Moreover, the density of ultraviolet rays produced was measured using an optical emission spectroscopy (OES). Then, $E.\ coli$ plated on agar medium was located a distance of 24 cm from the air outlet, and the sterilizing power was measured after 24 hours by observing the sterile halo.

As a result, the amount of anions generated was 145,000/$cm^3$, the concentration of ozone was 0.030 ppm or less, the amount of ultraviolet rays produced was about 2,800, and more than 99.9% of bacteria were sterilized.

Example 2

Figure 14:
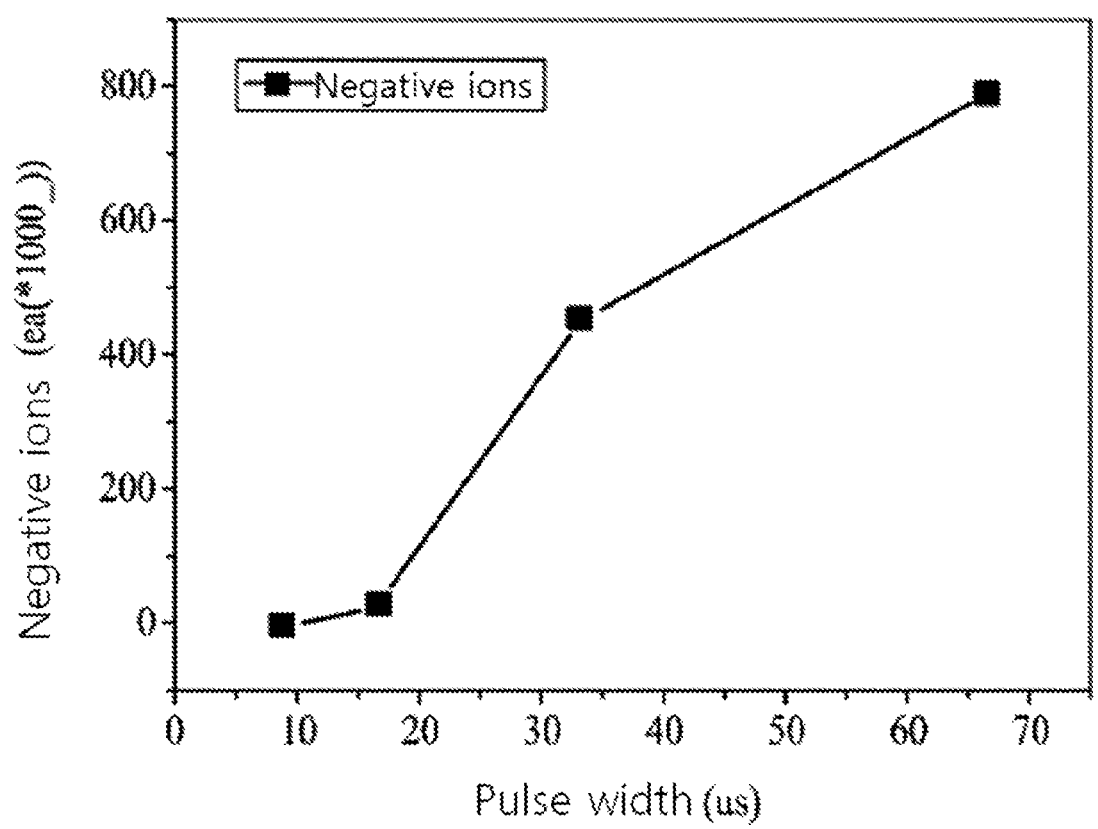
FIG. 14 shows the performance of a plasma electrode in accordance with an embodiment of the present invention.

The electric energy applied to the electrode, i.e., the number of anions generated with an increase in pulse width was measured and shown in FIG. 14. As shown in FIG. 14, it can be seen that the number of anions generated with an increase in pulse width was rapidly increased, and the number of anions was close to 1 million per cubic centimeter as the pulse width was close to 100 µs.

Comparative Example 1

Meanwhile, in a multiple needle electrode structure for comparison with the present invention, the amount of ultraviolet rays produced was about 300, which was about 10% of the present invention, the amount of anions generated was 1,450/$cm^3$, and the sterilizing effect was not significant even after 72 hours. Moreover, a voltage of 2 kV or more was applied to generate the plasma, which was very dangerous to handle and use.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A dielectric barrier discharge-type plasma generating electrode structure comprising:
   an upper conductive electrode and a lower conductive electrode;
   at least one conductive electrode protrusion formed on at least one inner surface of the upper conductive electrode and the lower conductive electrode facing each other;
   a dielectric layer formed with a substantially uniform thickness on at least one inner surface of the upper conductive electrode and the lower conductive electrode facing each other; and
   a predetermined gap d formed between the upper and lower conductive electrodes and the dielectric layer or between the dielectric layers facing each other due to the protrusion effect of the conductive electrode protrusion when the upper conductive electrode and the lower conductive electrode are brought into close contact with each other,
   wherein a pulse or AC power is applied to the upper conductive electrode and the lower conductive electrode to generate a plasma therebetween.

2. The dielectric barrier discharge-type plasma generating electrode structure of claim 1, wherein the pulse or AC power has a pulse width of 100 μs or less and a voltage of 1,000 V or less.

3. The dielectric barrier discharge-type plasma generating electrode structure of claim 1, wherein the electrode structure generates a plasma with a discharge current of 20 mA or less in the predetermined gaps d, d1, d2, and d3.

4. The dielectric barrier discharge-type plasma generating electrode structure of claim 1, wherein the conductive electrode protrusion is formed with a height of 1,000 μm or less.

5. The dielectric barrier discharge-type plasma generating electrode structure of claim 1, wherein the conductive electrode protrusion has at least one shape selected from the group consisting of a circular shape, a quadrangular shape, a polygonal shape, an oval shape, a star shape, and combinations thereof and is formed by at least one method selected from the group consisting of press processing, etching processing, welding processing, metal spacer attachment, metal molding processing, and combinations thereof.

6. The dielectric barrier discharge-type plasma generating electrode structure of claim 1, wherein the upper conductive electrode or the lower conductive electrode has a grid shape.

7. The dielectric barrier discharge-type plasma generating electrode structure of claim 1, wherein the electrode structure has a through hole formed in at least one position selected from the group consisting of the upper conductive electrode, the lower conductive electrode, and the dielectric layer, the through hole having at least one shape selected from the group consisting of a circular shape, a quadrangular shape, an oval shape, a polygonal shape, a star shape, other shapes and combinations thereof.

8. The dielectric barrier discharge-type plasma generating electrode structure of claim 1, wherein the dielectric layer is formed by at least one method selected from the group consisting of spraying, plasma spraying, coating, dipping, screen printing, and combinations thereof.

9. The dielectric barrier discharge-type plasma generating electrode structure of claim 1, wherein the electrode structure comprises one or more dielectric layers, the dielectric layers being made of the same or different materials.

10. The dielectric barrier discharge-type plasma generating electrode structure of claim 1, wherein the electrode structure further comprises at least one selected from the group consisting of a protective coating layer, another dielectric layer, and a special functional layer (an ozone removal functional layer, an odor removal functional layer, and an insulating layer) which are formed on at least one surface selected from the group consisting of a surface of the upper conductive electrode, a surface of the lower conductive electrode, and a surface of the dielectric layer.

11. The dielectric barrier discharge-type plasma generating electrode structure of claim 1, wherein the predetermined gaps d, d1, d2, and d3 are filled with at least one insulating layer made of at least one selected from the group consisting of ceramic, glass, polymer, and combinations thereof.

12. The dielectric barrier discharge-type plasma generating electrode structure of claim 1, wherein two or more electrode structures are arranged in series at intervals, insulated and brought into contact with each other, stacked by alternating electrical polarities, or arranged in parallel to each other.

13. A dielectric barrier discharge-type plasma generating electrode structure comprising:
   an upper conductive electrode, a lower conductive electrode, and an inner conductive electrode;
   at least one upper conductive electrode protrusion formed on at least one inner surface of the upper conductive electrode and the inner conductive electrode facing each other;
   at least one lower conductive electrode protrusion formed on at least one inner surface of the lower conductive electrode and the inner conductive electrode facing each other;
   an upper dielectric layer formed with a substantially uniform thickness on at least one inner surface of the upper conductive electrode and the inner conductive electrode facing each other;
   a lower dielectric layer formed with a substantially uniform thickness on at least one inner surface of the lower conductive electrode and the inner conductive electrode facing each other;
   a predetermined gap d1 formed between one of the upper and inner conductive electrodes and the upper dielectric layer or between the upper dielectric layers due to the protrusion effect of the upper conductive electrode protrusion when the upper conductive electrode and the inner conductive electrode are brought into close contact with each other; and
   a predetermined gap d2 formed between one of the lower and inner conductive electrodes and the lower dielectric layer or between the lower dielectric layers due to the protrusion effect of the lower conductive electrode protrusion when the lower conductive electrode and the inner conductive electrode are brought into close contact with each other;
   wherein a pulse or AC power is applied to the upper conductive electrode and the lower conductive electrode as one electrode and the inner conductive layer as a counter electrode to generate a plasma discharge between the predetermined gap d1 and the predetermined gap d2 at the same time.

14. The dielectric barrier discharge-type plasma generating electrode structure of claim 13, wherein the inner conductive electrode is separated into two layers, such as an upper inner conductive electrode and a lower inner conductive electrode, at least one separated surface conductive electrode protrusion is formed on at least one of the separated surfaces of the newly formed inner conductive electrodes, and a dielectric layer is further formed on at least one of the separated surfaces to form a predetermined gap d3 between the separated surfaces due to the effect of the separated surface conductive electrode protrusion, thus generating a plasma therein.

15. The dielectric barrier discharge-type plasma generating electrode structure of claim 13, wherein at least one of the upper conductive electrode, the lower conductive electrode, and the inner conductive electrode has a grid shape.

16. The dielectric barrier discharge-type plasma generating electrode structure of claim 13, wherein the electrode structure has a through hole formed in at least one position selected from the group consisting of the upper conductive electrode, the lower conductive electrode, the inner conductive electrode, and the dielectric layer, the through hole having at least one shape selected from the group consisting of a circular shape, a quadrangular shape, an oval shape, a polygonal shape, a star shape, other shapes and combinations thereof.

17. The dielectric barrier discharge-type plasma generating electrode structure of claim 13, wherein the electrode structure further comprises at least one selected from the group consisting of a protective coating layer, another dielectric layer, and a special functional layer (an ozone removal functional layer, an odor removal functional layer, and an insulating layer) which are formed on at least one surface selected from the group consisting of a surface of the upper conductive electrode, a surface of the lower conductive electrode, a surface of the inner conductive electrode, and a surface of the dielectric layer.

* * * * *